United States Patent
Fox et al.

(10) Patent No.: US 9,974,933 B2
(45) Date of Patent: *May 22, 2018

(54) TISSUE MODIFICATION METHODS AND APPARATUS

(71) Applicant: Hansa Medical Products, Inc., Carmel, IN (US)

(72) Inventors: Dart A. Fox, Indianapolis, IN (US); Eric D. Blom, Carmel, IN (US); Brian Kamradt, Indianapolis, IN (US)

(73) Assignee: HANSA MEDICAL PRODUCTS, INC., Carmel, IN (US)

( * ) Notice: Subject to any disclaimer, the term of this patent is extended or adjusted under 35 U.S.C. 154(b) by 0 days. days.

This patent is subject to a terminal disclaimer.

(21) Appl. No.: 15/463,006

(22) Filed: Mar. 20, 2017

(65) Prior Publication Data
US 2017/0189657 A1 Jul. 6, 2017

Related U.S. Application Data

(63) Continuation of application No. 15/181,311, filed on Jun. 13, 2016, now Pat. No. 9,604,042, which is a (Continued)

(51) Int. Cl.
*A61B 5/00* (2006.01)
*A61M 29/02* (2006.01)
(Continued)

(52) U.S. Cl.
CPC .............. *A61M 29/02* (2013.01); *A61F 2/12* (2013.01); *A61M 5/1452* (2013.01); (Continued)

(58) Field of Classification Search
CPC .................. A61M 29/02; A61M 25/10; A61M 25/10181; A61M 25/10184; A61M 25/104; A61F 2/12
See application file for complete search history.

(56) References Cited

U.S. PATENT DOCUMENTS 5,152,776 A 10/1992 Pinchuk
5,273,537 A 12/1993 Haskvitz et al.
(Continued)

FOREIGN PATENT DOCUMENTS

EP 1617893 1/2006
WO 2004093966 A1 11/2004
WO 2007002154 A2 1/2007

OTHER PUBLICATIONS

International Search Report from related PCT/US2014/47400 dated Jan. 22, 2015, 9 pages.
Extended European Search Report, European Application No. 14844573.7-1501/3043859, dated Apr. 11, 2017, 6 pages.

*Primary Examiner* — Max Hindenburg
(74) *Attorney, Agent, or Firm* — Barnes & Thornburg LLP

(57) ABSTRACT

A method and apparatus for treating a stricture in a body lumen. The method comprises (a) sensing pressure being exerted by a treatment device on the stricture, (b) determining if enough force is being exerted on the stricture, (c) if enough force is being exerted on the stricture, timing the application of enough force, (d) determining if too much force is being exerted by the treatment device on the stricture, (e) if too much force is being applied to the stricture, decrementing the force being applied to the stricture, (f) determining if not enough force is being applied to the stricture, (g) if not enough force is being applied to the stricture incrementing the force being applied to the stricture, and (h) repeating (a)-(g) until (i) a desired pressure has been maintained on the tissue for a desired time. The apparatus comprises a device for exerting pressure on the stricture, a controller for controlling the amount of pressure the device exerts on the stricture, and a pressure sensor for sensing the pressure being exerted on the stricture by the device.

3 Claims, 24 Drawing Sheets

Related U.S. Application Data continuation of application No. 14/024,835, filed on Sep. 12, 2013, now Pat. No. 9,375,556.

(51) Int. Cl.
*A61M 25/10* (2013.01)
*A61M 5/145* (2006.01)
*A61F 2/12* (2006.01)
*A61F 2/48* (2006.01)

(52) U.S. Cl.
CPC ............... *A61M 25/10182* (2013.11); *A61M 25/10184* (2013.11); *A61F 2002/485* (2013.01); *A61F 2002/487* (2013.01); *A61F 2250/0096* (2013.01); *A61M 2205/3344* (2013.01)

(56) References Cited

U.S. PATENT DOCUMENTS

| | | |
|---|---|---|
| 6,338,726 B1 | 1/2002 | Edwards et al. |
| 7,641,448 B2 | 1/2010 | Gydesen |
| 8,147,511 B2 | 4/2012 | Perry et al. |
| 8,628,555 B2 | 1/2014 | Perry et al. |
| 9,375,556 B2 | 6/2016 | Fox et al. |
| 9,604,042 B2 | 3/2017 | Fox et al. |
| 2004/0230157 A1 | 11/2004 | Perry et al. |
| 2007/0197963 A1 | 8/2007 | Griffiths et al. |
| 2009/0312740 A1 | 12/2009 | Kim et al. |
| 2010/0022824 A1 | 1/2010 | Cybulski et al. |
| 2010/0113939 A1 | 5/2010 | Mashimo et al. |
| 2012/0259217 A1 | 10/2012 | Gerrans et al. |

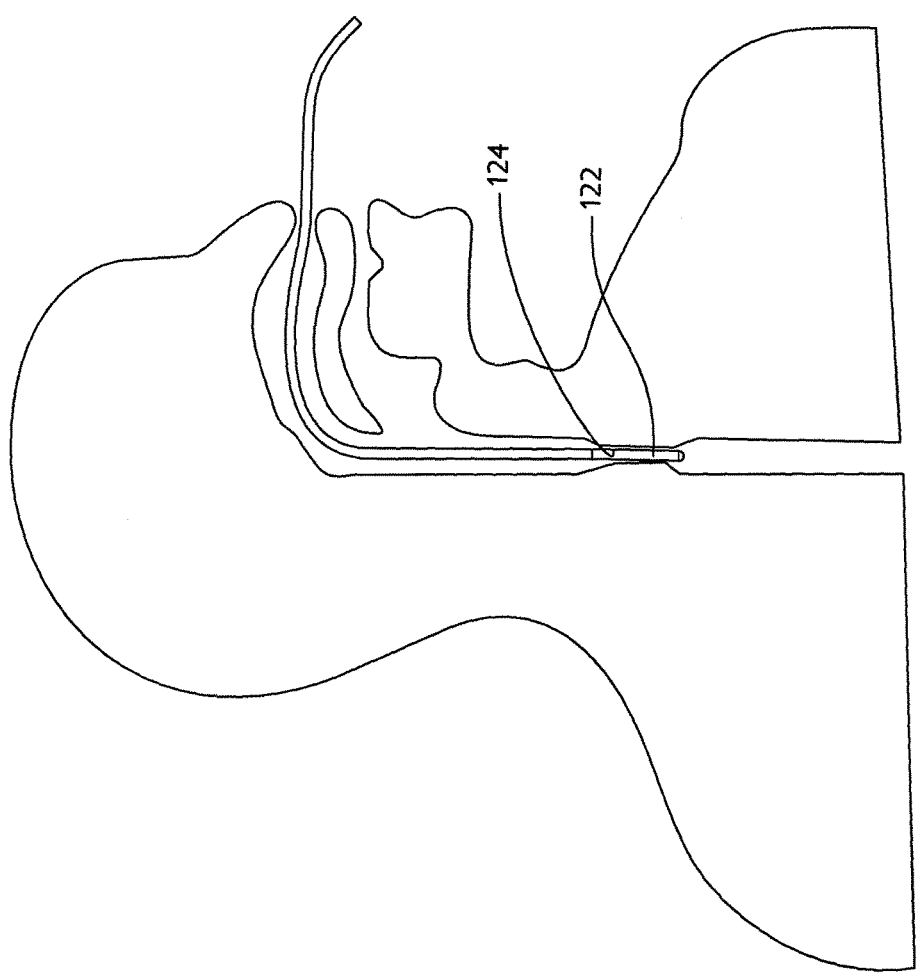

TISSUE MODIFICATION METHODS AND APPARATUS

This application claims to U.S. patent application Ser. No. 15/181,311, now U.S. Pat. No. 9,604,042, which claimed priority to U.S. patent application Ser. No. 14/024,835, now U.S. Pat. No. 9,375,556, which was filed on Sep. 12, 2013 and is expressly incorporated herein by reference.

BACKGROUND

Surgical procedures are frequently performed on human and animal body lumens. For example, laryngectomies involve the esophagus and the trachea. Such procedures often result in the formation of strictures of scar tissue as the surgical sites heal. In many cases, these strictures can continue to grow, progressively occluding the affected lumen(s). Attention to such sites is necessary to maintain the lumen(s) patent. Chemotherapy and radiation therapy can cause such strictures to form, as can acid reflux disease. These also typically require attention.

In the past, surgical patients who experienced the growth of such strictures checked into the healthcare facility, typically a hospital or surgical center, were placed under anesthesia, and had their strictures broken open. This, of course, required recovery not only from anesthesia but also from the sometimes traumatic breaking open of the stricture. Such a patient might remain in the surgical center for several hours, or the hospital overnight. Usually, the breaking open of the stricture would be done by rapidly inflating a balloon of a balloon catheter which had been located in the stricture, either visually or by imaging means, such as X-ray, CT, endoscopy or the like. Alternatively, the surgeon might use a series of bougies, passing bougies of increasing size through the stricture until it would pass one of sufficient size to alleviate the problems associated with the stricture. This, of course, requires essentially continuous involvement by the surgeon as the bougies of increasing size are passed through the stricture, stretching or breaking it. The surgeon would then have to attend to whatever trauma resulted from this treatment.

In another tissue modification application, patients who are undergoing, for example, breast remodeling surgery, burn surgery, or other types of surgery requiring skin grafts, are often treated to produce the required skin, so-called autologous grafts, for the remodeling or other surgery themselves.

SUMMARY

According to an aspect of the invention, a stricture is modified incrementally by either fluid (pneumatic or hydraulic) means or by mechanical means. The fluid means typically comprises a balloon catheter which is supplied either with a gas or mixture of gases, typically, compressed air, or a liquid, typically, a saline solution, perhaps containing a radiopaque contrast medium where that is desired.

The mechanical means typically includes multiple flexible ribs which are flexed outwardly by an actuator against the tissue, or a cylindrical, helically wound braid, such as a biaxial braid, or so-called "Chinese handcuffs." Illustratively, the material is TechFlex FlexoPET brand braid. However, stainless steel or other material braid may be used as appropriate. The material from which the ribs or braid are constructed may be treated to reduce microbial population, may be coated with a thin membrane, or may be sterilizable. The ribs or braid are used "in reverse." That is, an actuator, such as a control wire, extends through the interior of the assembly of ribs or the braid so that tension on the wire causes the cross sectional area of the assembly of ribs or the body of the braid (transverse to the longitudinal extent of the assembly of ribs or braid and transverse to the direction of pull of the control wire) to increase. In use according to the invention, the assembly of ribs or braid is placed in the stricture so that the increasing cross sectional area or cross sectional aspect exerts a stretching force on the stricture, enlarging it and relieving the patient's symptoms.

In order to reduce the trauma associated with the treatment of strictures, and in order to reduce the amount of the attending physician's time necessary for treatment, a programmable controller incrementally controls the inflation of the balloon, in the case of the pneumatic or hydraulic devices, or the enlargement of the cross section of the mechanical device, in the case of the mechanical device.

According to an aspect of the invention, skin for remodeling, such as breast reconstructions, can be promoted by implanting under the skin of a patient either the fluid (pneumatic or hydraulic) device or the mechanical device. The device (or devices of different sizes) is (are) then enlarged incrementally, causing the patient to produce additional skin either for subsequent harvesting for (a) graft(s) or so that the remodeling can be conducted and there will be sufficient skin to cover it.

According to an aspect of the invention, a method for treating a stricture in a body lumen comprises (a) sensing pressure being exerted by a treatment device on the stricture, (b) determining if enough force is being exerted on the stricture, (c) if enough force is being exerted on the stricture, timing the application of enough force, (d) determining if too much force is being exerted by the treatment device on the stricture, (e) if too much force is being applied to the stricture, decrementing the force being applied to the stricture, (f) determining if not enough force is being applied to the stricture, (g) if not enough force is being applied to the stricture incrementing the force being applied to the stricture, and (h) repeating (a)-(g) until (i) a desired pressure has been maintained on the tissue for a desired time.

According to an aspect of the invention, apparatus for treating a stricture in a body lumen comprising a device for exerting pressure on the stricture, a controller for controlling the amount of pressure the device exerts on the stricture, and a pressure sensor for sensing the pressure being exerted on the stricture by the device.

Illustratively according to this aspect, the device includes a syringe, an inflating fluid and a balloon catheter. The inflating fluid inflates the balloon of the catheter in the stricture incrementally, gradually relieving the stricture.

Illustratively according to this aspect, the device includes a motor, a screw coupled to the motor, and a follower for following rotation of the screw to advance and retract a plunger of the syringe to increase and decrease, respectively, the pressure of the inflating fluid in the balloon.

Alternatively illustratively according to this aspect, the device includes a mechanical expanding device. A proximal end of a control wire is coupled through a sheath to the device. Movement of the device moves the control wire, moving the distal end of the device toward the proximal end of the device, reducing the length of the device and increasing the device's cross sectional area or cross sectional aspect transverse to the length in the stricture incrementally, gradually relieving the stricture.

Illustratively according to this aspect, the device includes a motor which drives a screw, a follower for following rotation of screw to advance and retract the control wire to decrease and increase, respectively, the pressure of the device on the stricture.

Illustratively according to this aspect, the device includes a limit switch to limit the pressure exerted by the device on the stricture.

According to an aspect of the invention, a method for remodeling tissue in a body comprises (a) sensing pressure being exerted by a treatment device on the tissue, (b) determining if enough pressure is being exerted by the device, (c) if enough pressure is being exerted by the device, timing the application of enough pressure, (d) determining if too much pressure is being exerted by the device, (e) if too much pressure is being exerted by the device, decrementing the pressure being exerted by the device, (f) determining if not enough pressure is being exerted by the device, (g) if not enough pressure is being exerted by the device incrementing the pressure being exerted by the device, and (h) repeating (a)-(g) until (i) a desired pressure has been maintained on the tissue for a desired time.

According to an aspect of the invention, apparatus for remodeling tissue in a body comprises a device for exerting pressure on the tissue, a controller for controlling the amount of pressure the device exerts on the tissue, and a pressure sensor for sensing the pressure being exerted on the tissue by the device.

Illustratively according to this aspect, the device includes a syringe, an inflating fluid and a balloon catheter. The inflating fluid inflates the balloon of the catheter adjacent the tissue incrementally, gradually remodeling the tissue.

Illustratively according to this aspect, the device includes a motor, a screw coupled to the motor, and a follower for following rotation of the screw to advance and retract a plunger of the syringe to increase and decrease, respectively, the pressure of the inflating fluid in the balloon.

Alternatively illustratively according to this aspect, the device includes a braid, a proximal end of a control wire coupled through a sheath to the device. Movement of the device moves the control wire, moving the distal end of the device toward the proximal end of the device, reducing the length of the device and increasing the device's cross section transverse to the length adjacent the tissue incrementally, gradually remodeling the tissue.

Illustratively according to this aspect, the device includes a motor which drives a screw, a follower for following rotation of screw to advance and retract the control wire to decrease and increase, respectively, the pressure of the device on the tissue.

Illustratively according to this aspect, the device includes a limit switch to limit the pressure exerted by the device on the tissue.

BRIEF DESCRIPTION OF THE DRAWINGS

The invention may best be understood by referring to the following detailed description and accompanying drawings which illustrate the invention. In the drawings:

FIG. 6 illustrates the deflated balloon catheter of FIG. 4 oriented in an esophageal stricture;

DETAILED DESCRIPTIONS OF ILLUSTRATIVE EMBODIMENTS

Figure 1:
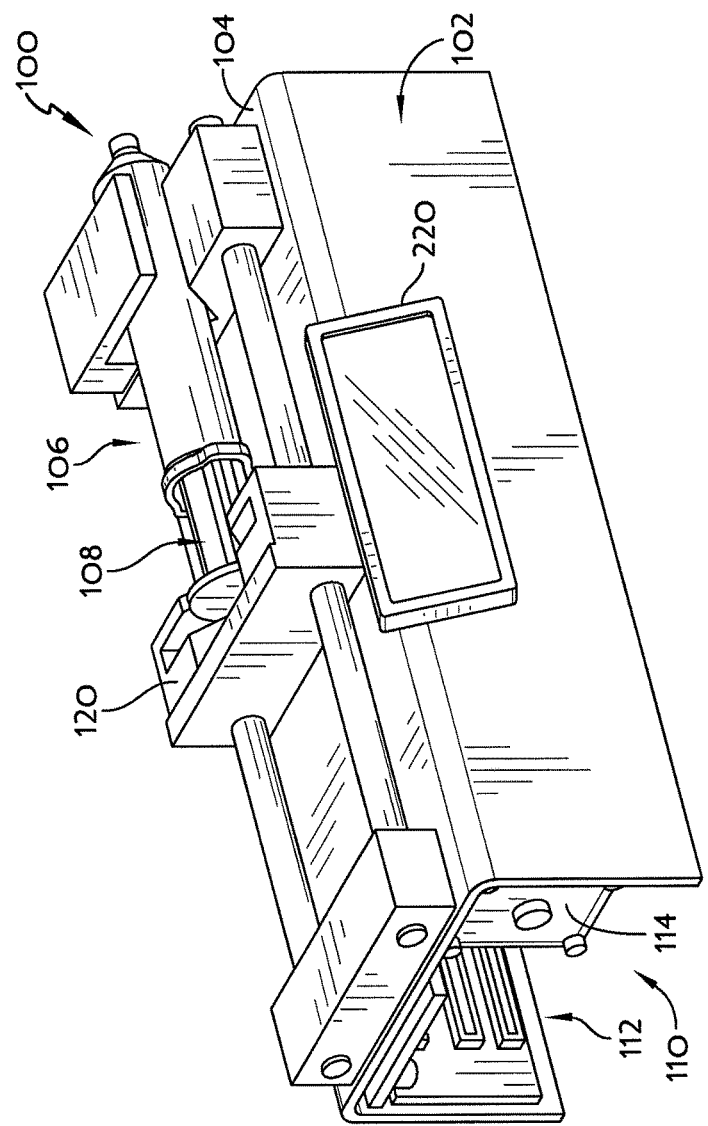
FIG. 1 illustrates a perspective view of a syringe pump constructed according to the invention.
Figure 2:
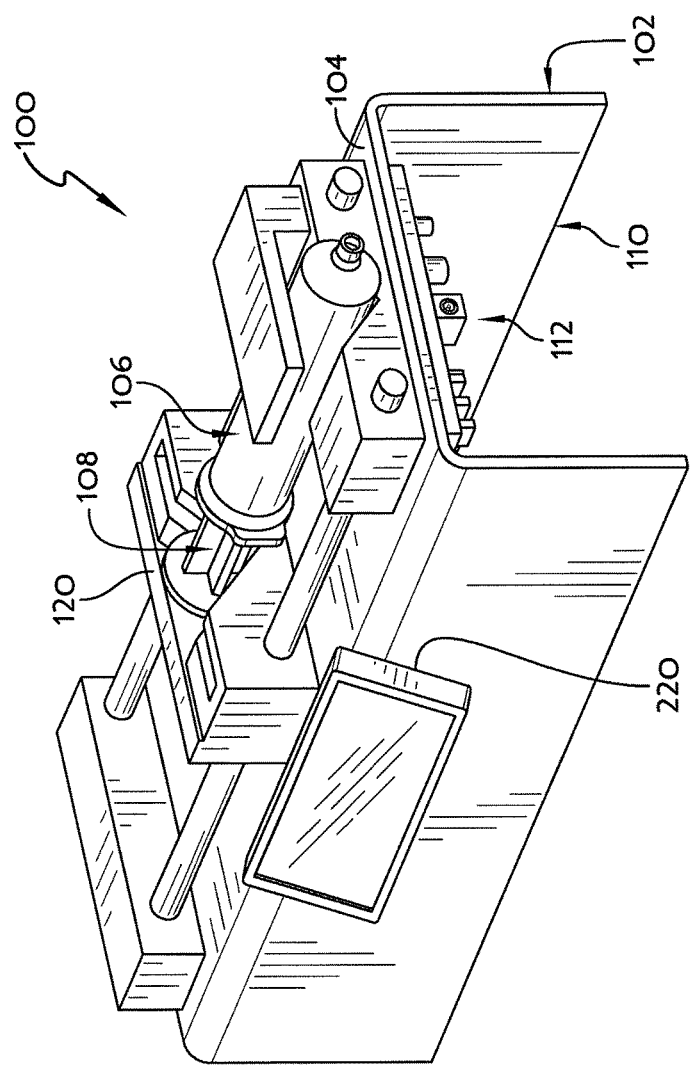
FIG. 2 illustrates a perspective view of the syringe pump illustrated in FIG. 1, taken from the opposite end of the pump.
Figure 3:
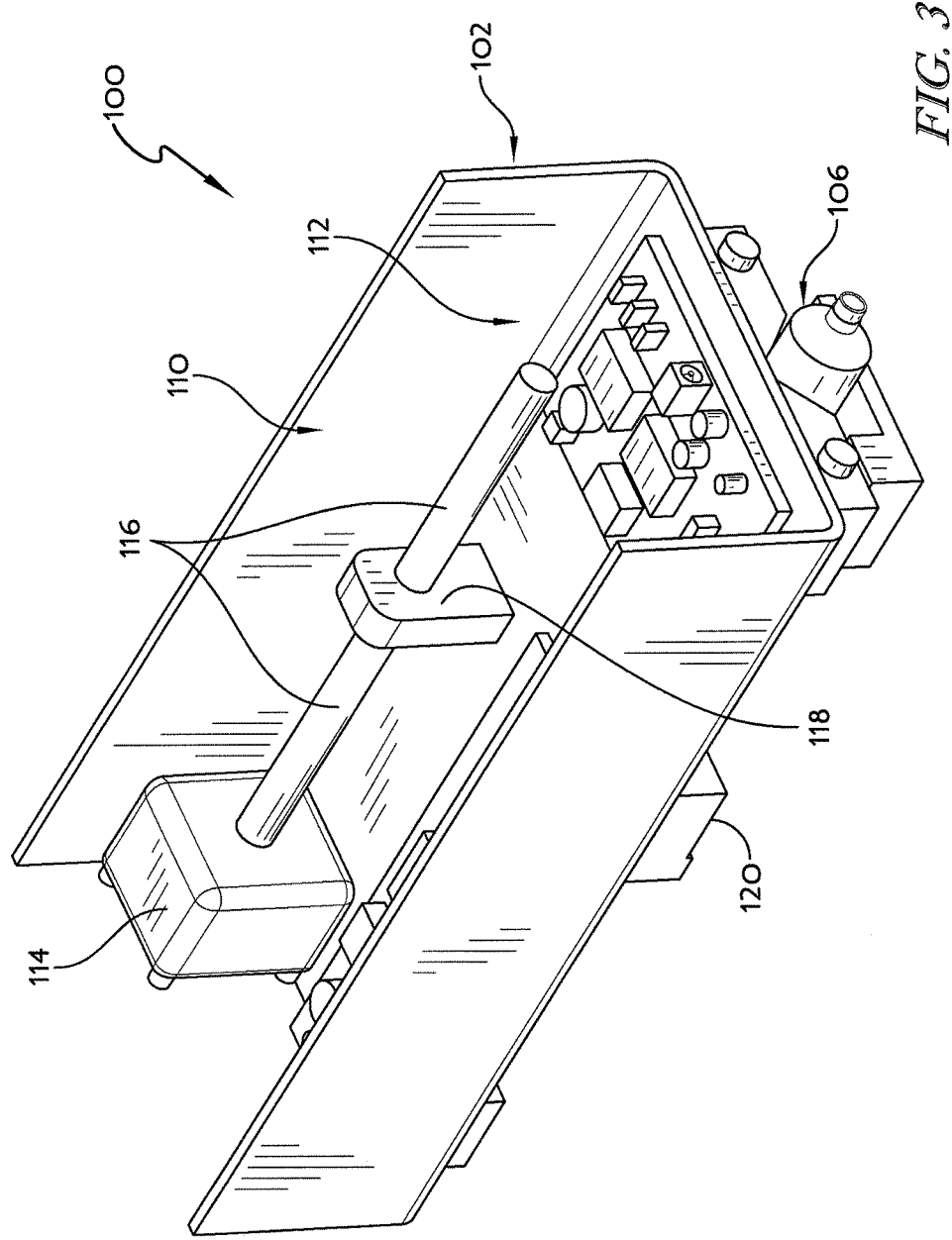
FIG. 3 illustrates a perspective view from the underside of the pump illustrated in FIGS. 1-2.

Referring now to FIGS. 1-11 and 22-24, the apparatus includes a syringe pump 100, such as, for example, a New Era model NE-510X syringe pump available from New Era Pump Systems, Farmingdale, N.Y. Pump 100 includes an inverted U-shaped chassis 102 providing a top surface 104 upon which the syringe 106 is clamped and its plunger 108 manipulated, and an underside 110 for housing the electronics 112 for controlling the pump 100 are mounted. The electronics 112 include a stepper motor 114, such as, for example, a Coact Model 17H185H-15P stepper motor, which drives a screw 116 (FIG. 3) on its output shaft. A follower, or linear slide, 118 follows the rotation of the screw 116 to advance and retract (depending upon the direction of motor rotation) a block 120 into which the plunger 108 is inserted. In this way, rotation of the motor 114 drives the plunger 108 under control of the electronics 112 which control the motor 114.

Figure 4:
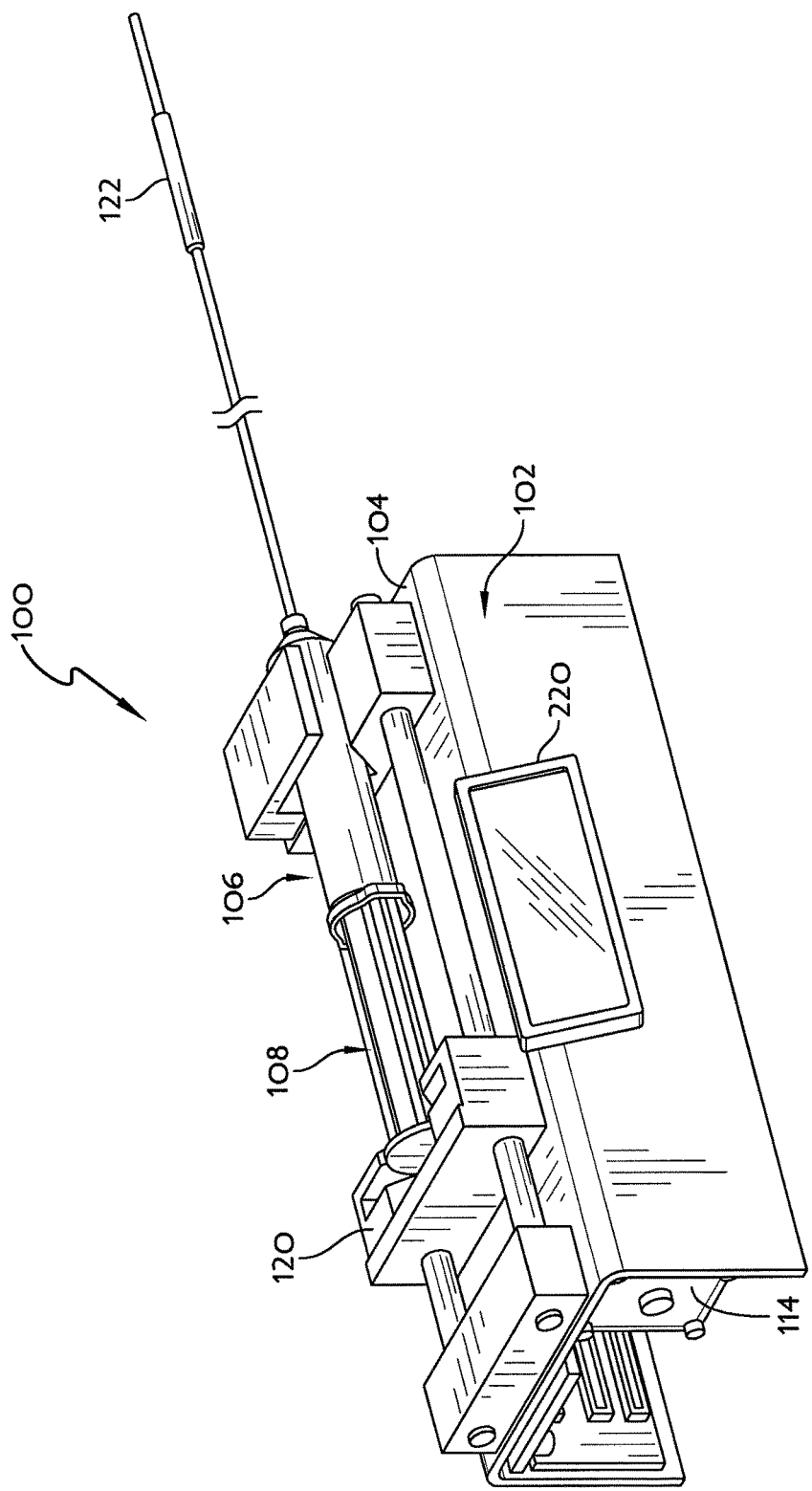
FIG. 4 illustrates a view similar to FIG. 1, but with a balloon catheter fitted to the syringe of the pump.
Figures 5, 5A:
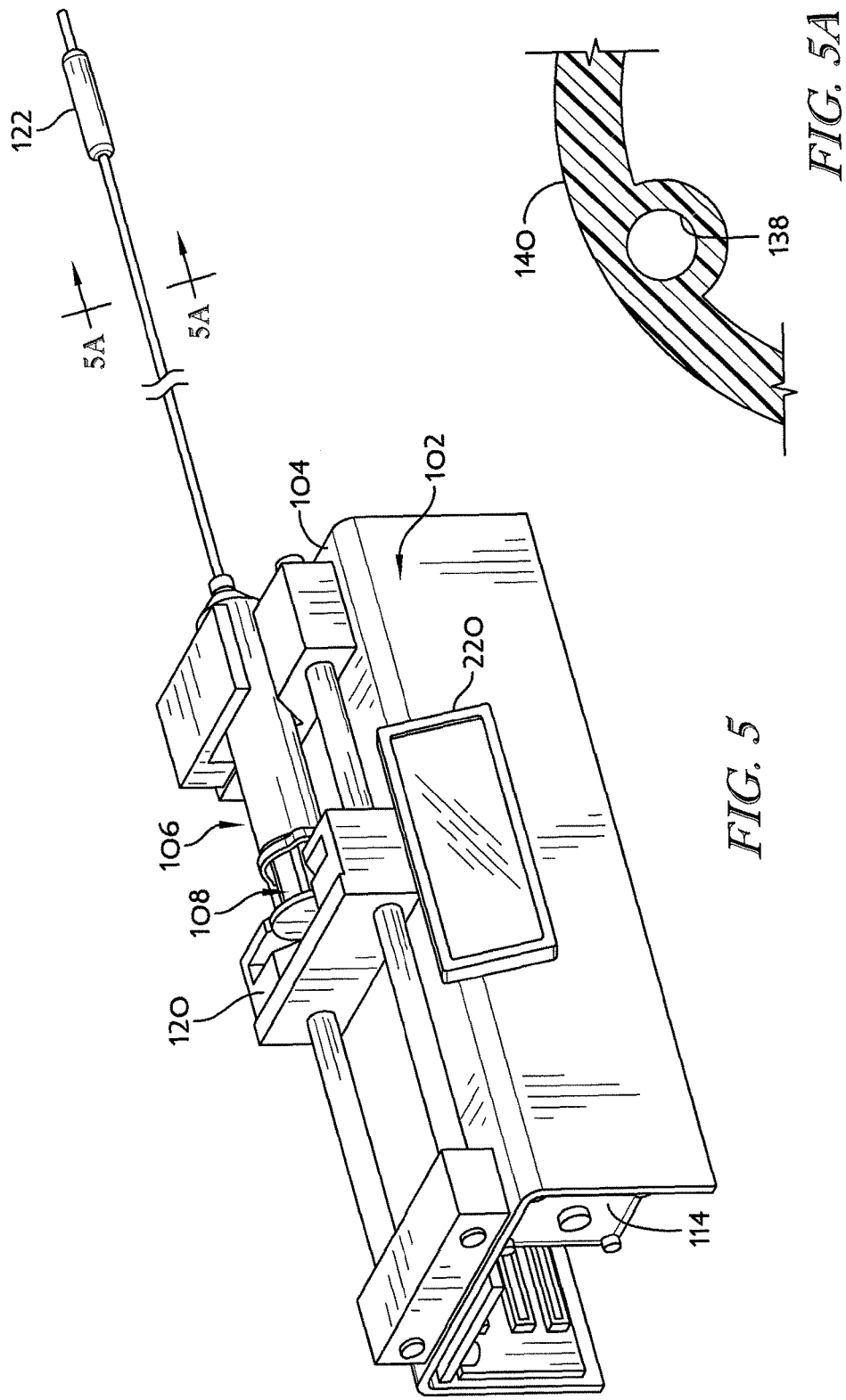
FIG. 5 illustrates a view similar to FIG. 4, but with the balloon inflated.
FIG. 5A illustrates a somewhat enlarged fragmentary sectional view of FIG. 5 taken along section lines 5A-5A thereof.
Figure 7:
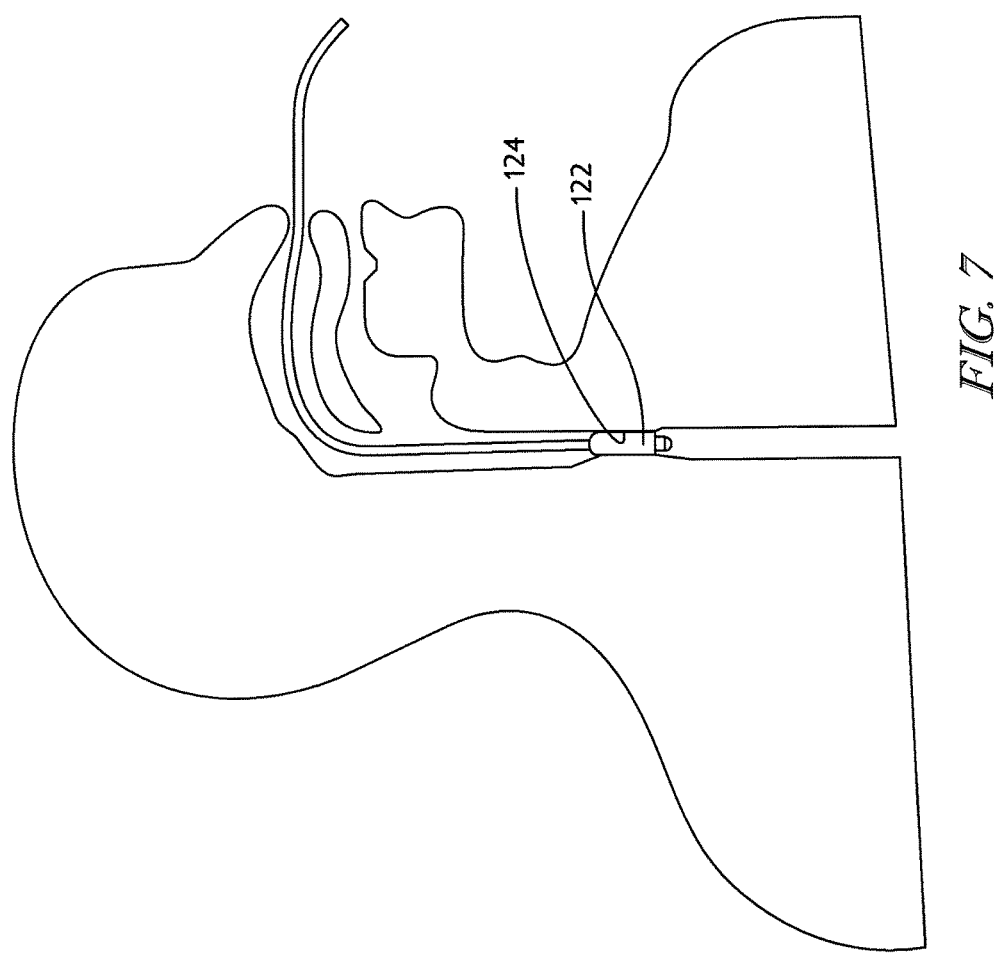
FIG. 7 illustrates the balloon inflated in the stricture.
Figure 8:
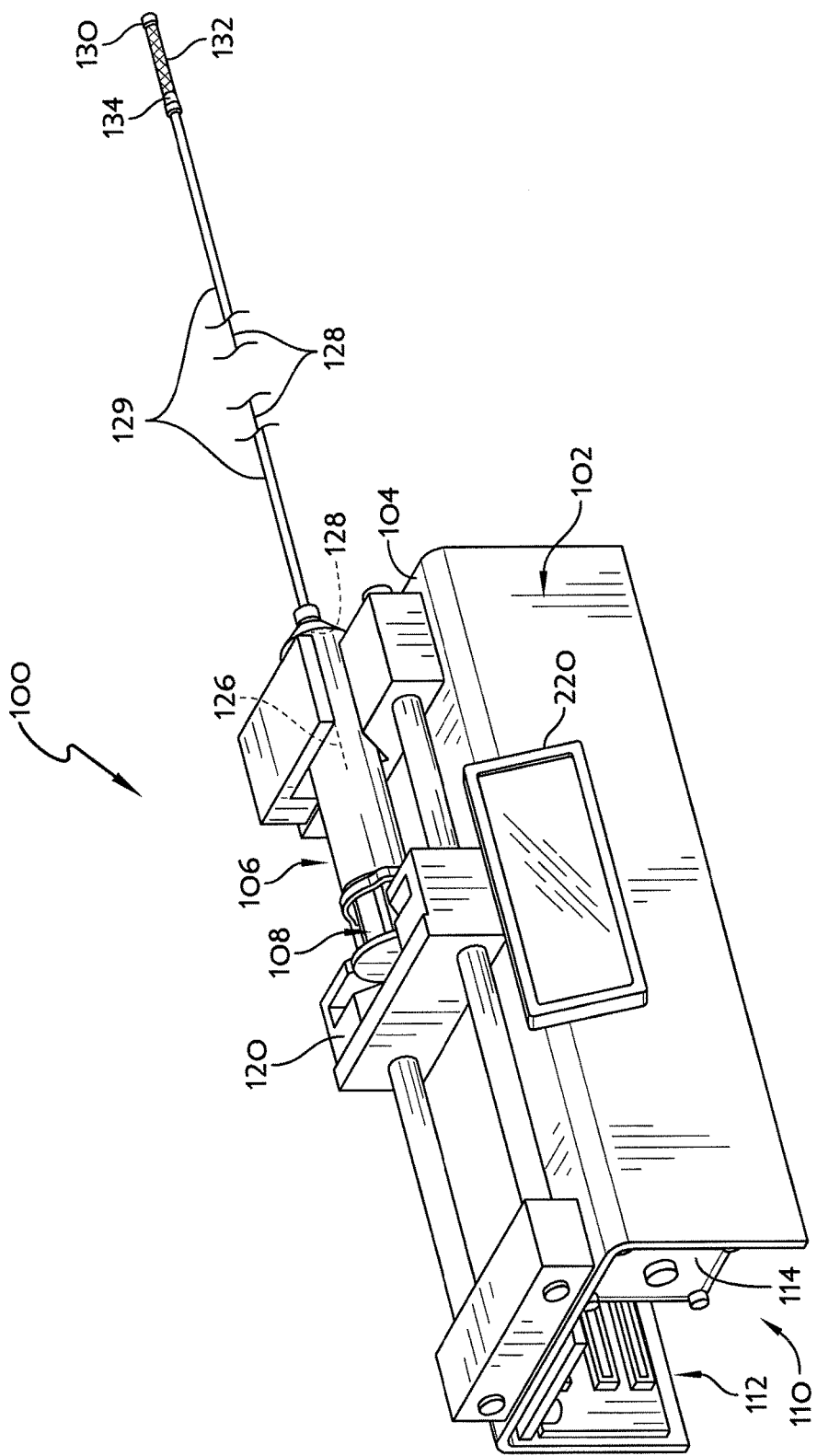
FIG. 8 illustrates a view similar to FIG. 1, but with a cylindrical, helically wound braid tipped sheathed control wire fitted to the syringe of the pump.
Figure 9:
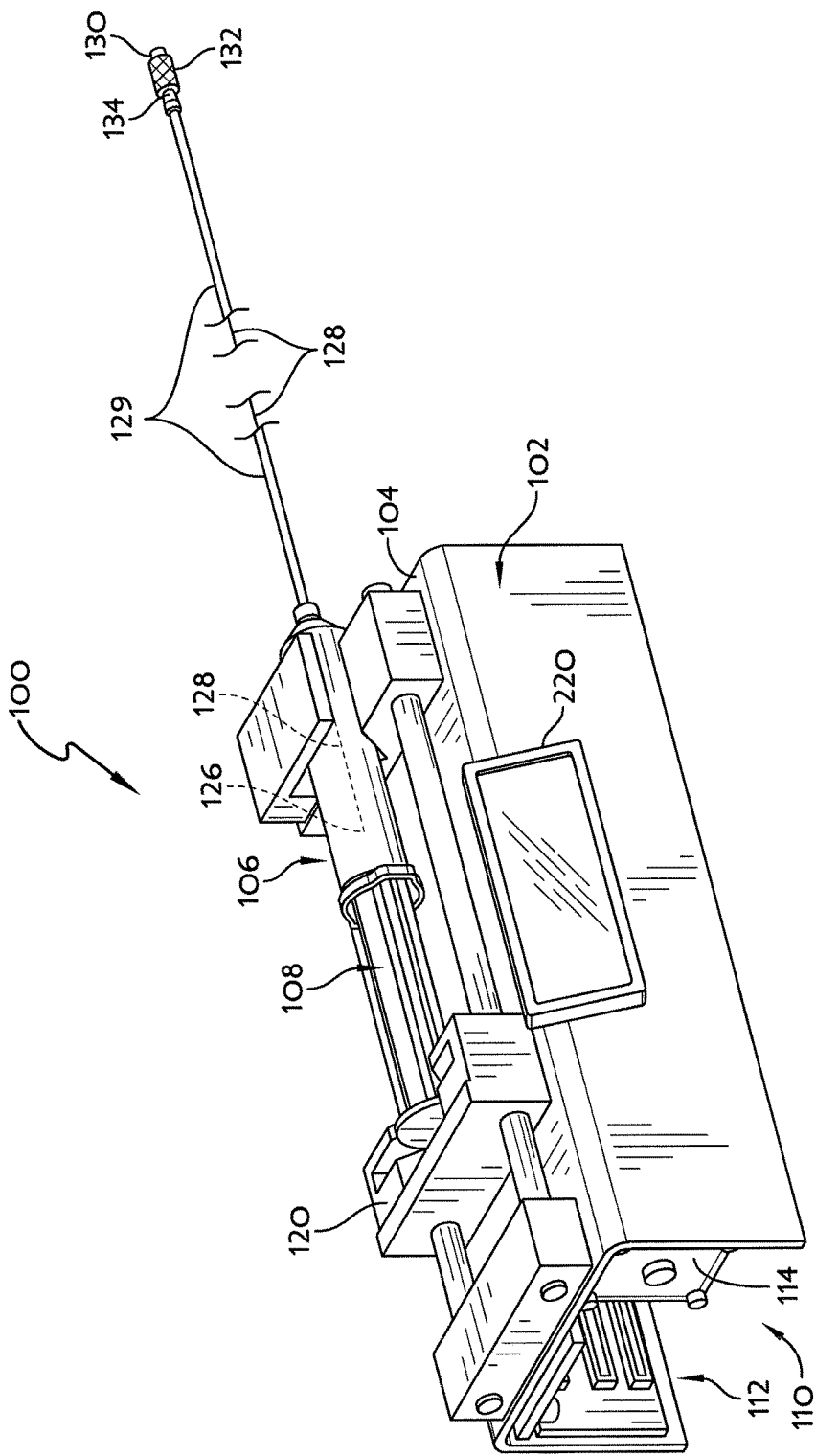
FIG. 9 illustrates a view similar to FIG. 8, but with the braid tip expanded.
Figure 10:
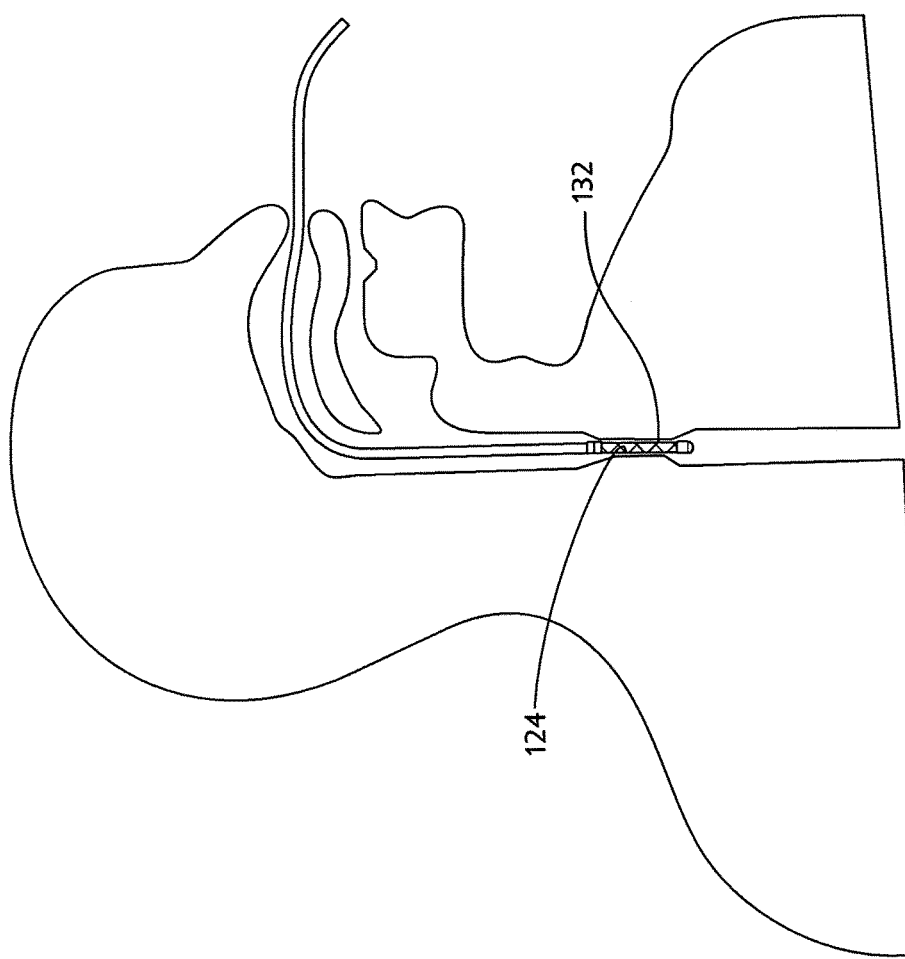
FIG. 10 illustrates the unexpanded braid tip of FIG. 8 oriented in an esophageal stricture.
Figure 11:
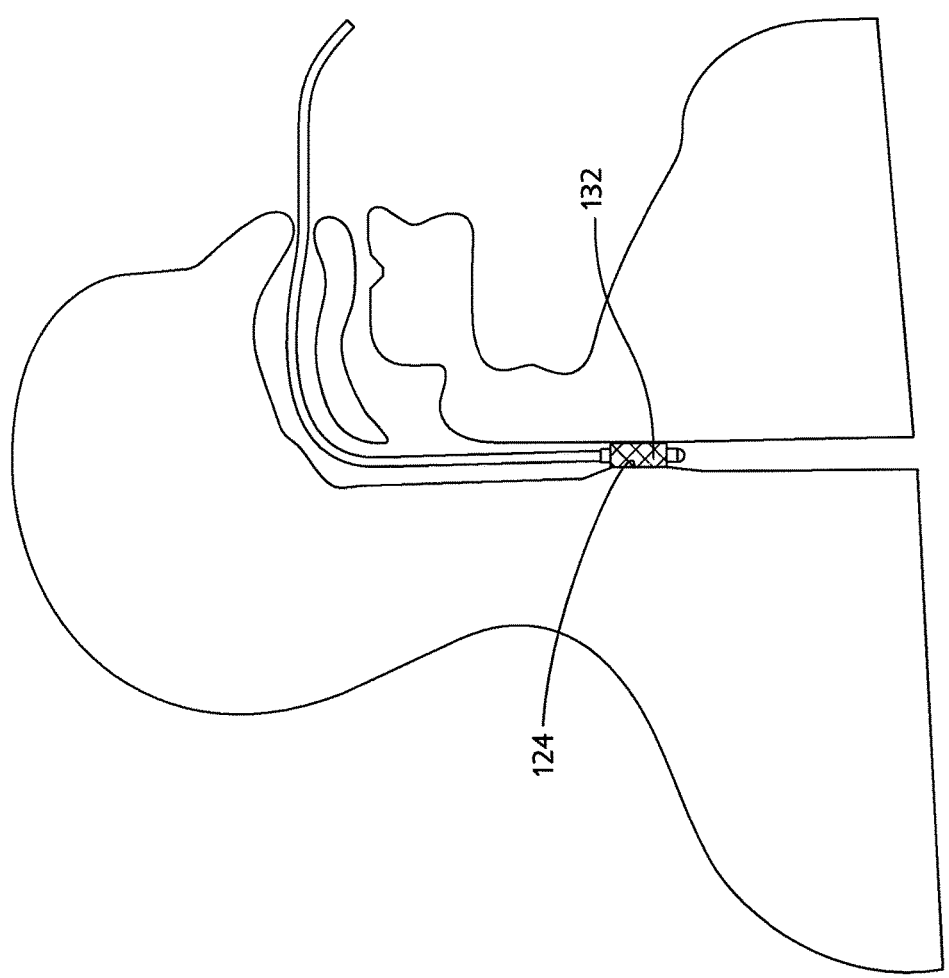
FIG. 11 illustrates the expanded braid tip in the stricture.
Figure 12:
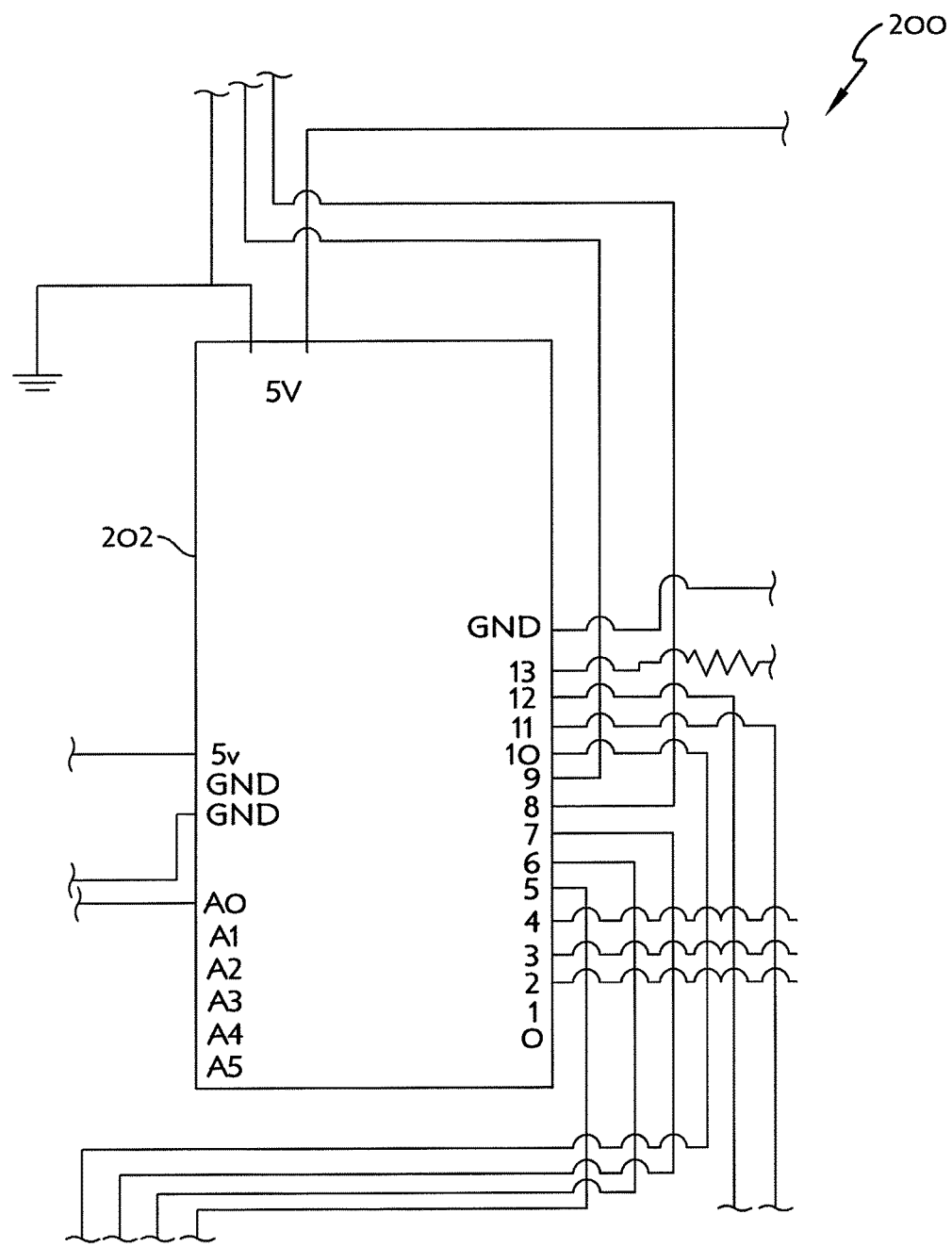
FIGS. 12-17 illustrate electrical circuit diagram of a controller useful to practice the invention.
Figure 24:
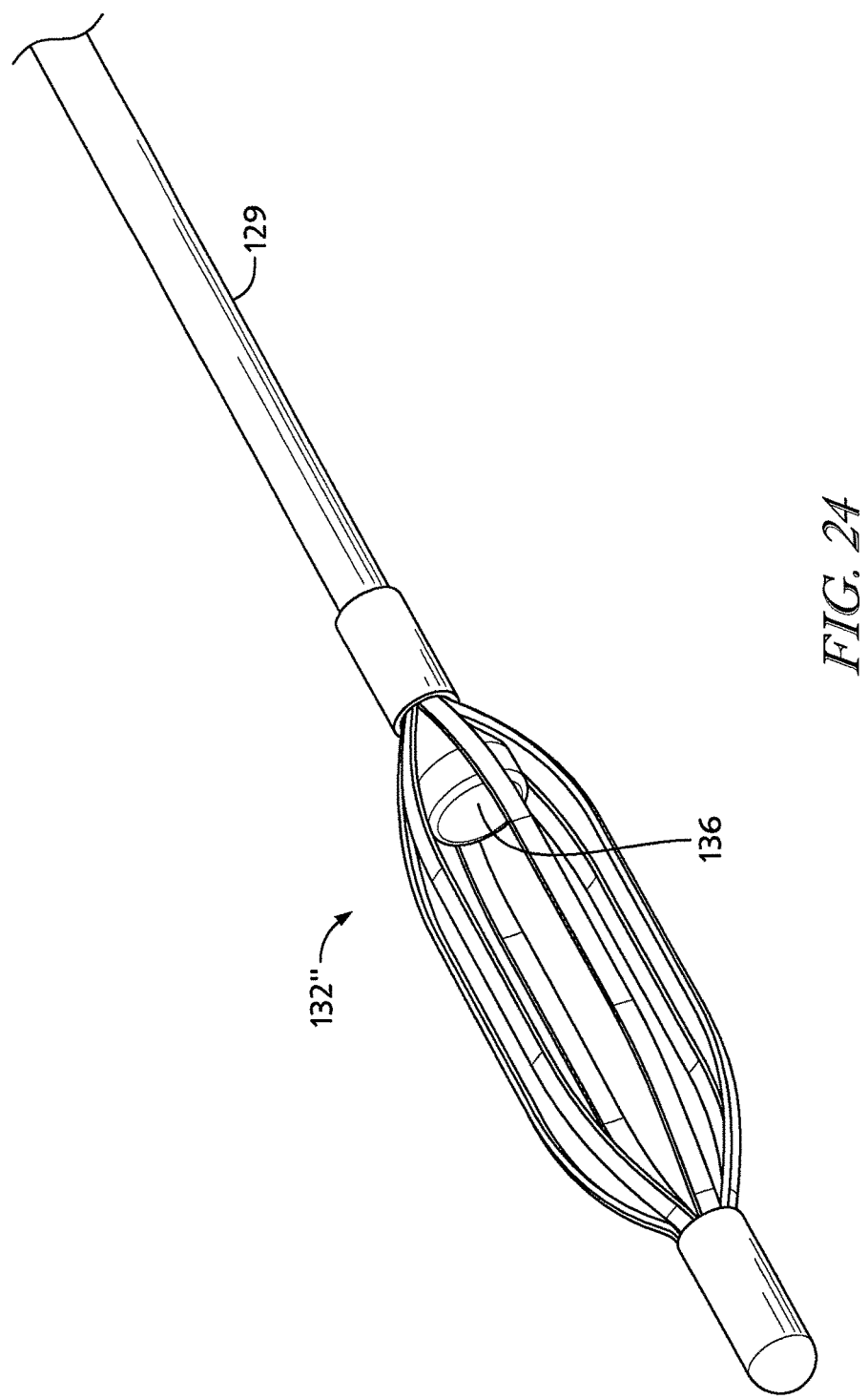

In balloon catheter embodiments FIGS. 4-7, the plunger 108 forces an inflating fluid, typically air or water, out of the syringe 106 into the balloon 122, compare FIGS. 4 and 6 with FIGS. 5 and 7, to inflate the balloon 122 in the stricture 124 incrementally, gradually relieving the stricture 124. In the mechanical device embodiments, FIGS. 8-11 and 22-24, a proximal end 126 of a control wire 128 is coupled through a sheath 129 to the plunger 108. Withdrawal of the plunger 108 from the barrel of the syringe 106 thus results in pulling of the control wire 128. In braid embodiments, the control wire 128 pulls the distal end 130 of the braid 132 toward the braid 132's proximal end 134, reducing its length and increasing its cross section transverse to its length in the stricture 124, compare FIGS. 8 and 10 with FIGS. 9 and 11, incrementally compressing and gradually relieving the stricture 124. In wire rib embodiments, the control wire 128' pulls the distal end 130' of the rib assembly 132' toward the rib assembly 132's proximal end 134', reducing its length and increasing its cross section transverse to its length in the stricture 124, compare FIG. 22 with FIG. 23, incrementally compressing and gradually relieving the stricture 124. As illustrated in FIG. 24, a distal end of control wire 128 can be provided with an enlargement 136 to spread the rib assembly 132" in the stricture 124, instead of having the control wire 128, 128' anchored to the distal end 130, 130' of the rib assembly 132, 132'.

The control wire 128 may be part of a bundle extending down the interior of the sheath 129, the bundle including multiple optical fibers which permit the introduction of light adjacent the distal end 130, 130' of the balloon 122, braid 132, or rib assembly 132', at the tip of the catheter, and the recovery of images of the stricture 124 site. With reference to FIG. 5A, in balloon or mechanical embodiments, an additional, small cross sectional area channel 138 can be provided in the catheter wall 140. An access port can be provided at the syringe pump 100 end and an exit port adjacent the balloon 122 or mechanical device 132, 132'. This channel 138 permits the introduction at the syringe pump 100 end of, for example, a topical anesthetic, a steroid, or other treatment substance, which is dispensed adjacent the balloon 122 or mechanical device 132, 132' to desensitize or treat tissue adjacent the stricture 124, if that is necessary or desirable. This dispensing can either be by aerosol or by threading a fine needle down the channel 138 and injecting the medical substance adjacent the stricture 124.

The schematic and block circuit diagram descriptions that follow identify specific integrated circuits and other components and in many cases specific sources for these. Specific terminal and pin names and numbers are generally given in connection with these for the purposes of completeness. It is to be understood that these terminal and pin identifiers are provided for these specifically identified components. It is to be understood that this does not constitute a representation, nor should any such representation be inferred, that the specific components, component values or sources are the only components available from the same or any other sources capable of performing the necessary functions. It is further to be understood that other suitable components available from the same or different sources may not use the same terminal/pin identifiers as those provided in this description.

Figure 13:
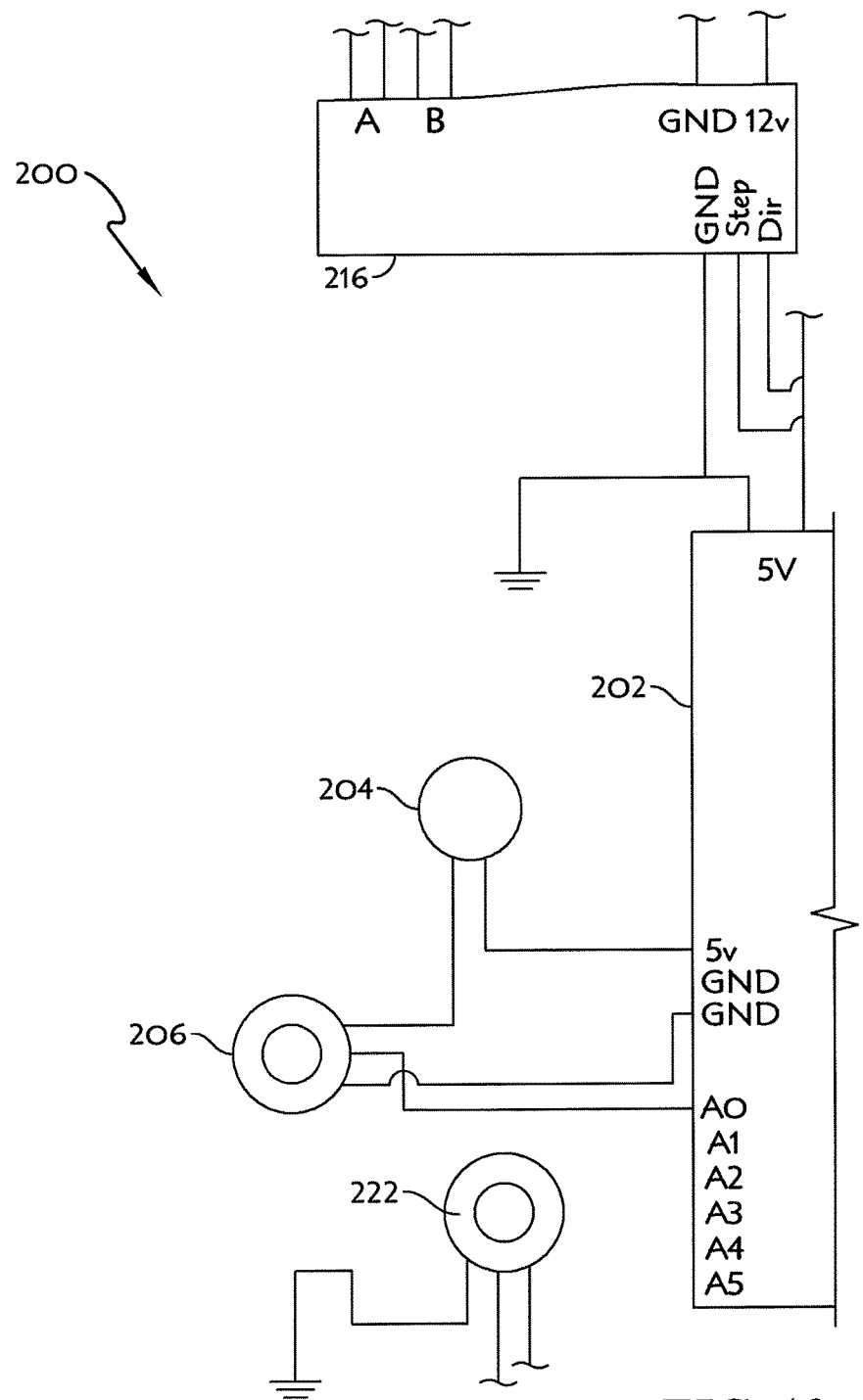

Referring now to FIGS. 12-17, an electrical block and schematic diagram of the controller 200, a microcontroller (µC) 202, FIGS. 12-16, has its 5V input terminal coupled to a terminal of a pressure sensor 204, FIG. 13, such as, for example, the Sparkfun Electronics (Tekscan) Flexiforce model A401 or SEN11207 pressure sensor 204. Pressure sensor 204 is positioned between facing surfaces of the plunger 108 and block 120 to sense pressure between these surfaces, and thereby, pressure on the stricture 124. µC 202 illustratively is an Arduino Uno µC or an Atmel 8-bit, AVR, RISC-based ATmega328P µC. The other terminal of pressure sensor 204 is coupled to a terminal of a 10 KΩ rotary potentiometer 206, illustratively, a linear taper model 271-1715. Another terminal of potentiometer 206 is coupled to a GrouND terminal of µC 202. Another terminal of potentiometer 206 is coupled to the A0 terminal of µC 202. Potentiometer 206 permits fine pressure adjustment. The resistance across the series combination of pressure sensor 204 and potentiometer 206 is monitored across the A0 and GND terminals of µC 202. This is a measure of the pressure being exerted on sensor 204 by plunger 108.

Figure 14:
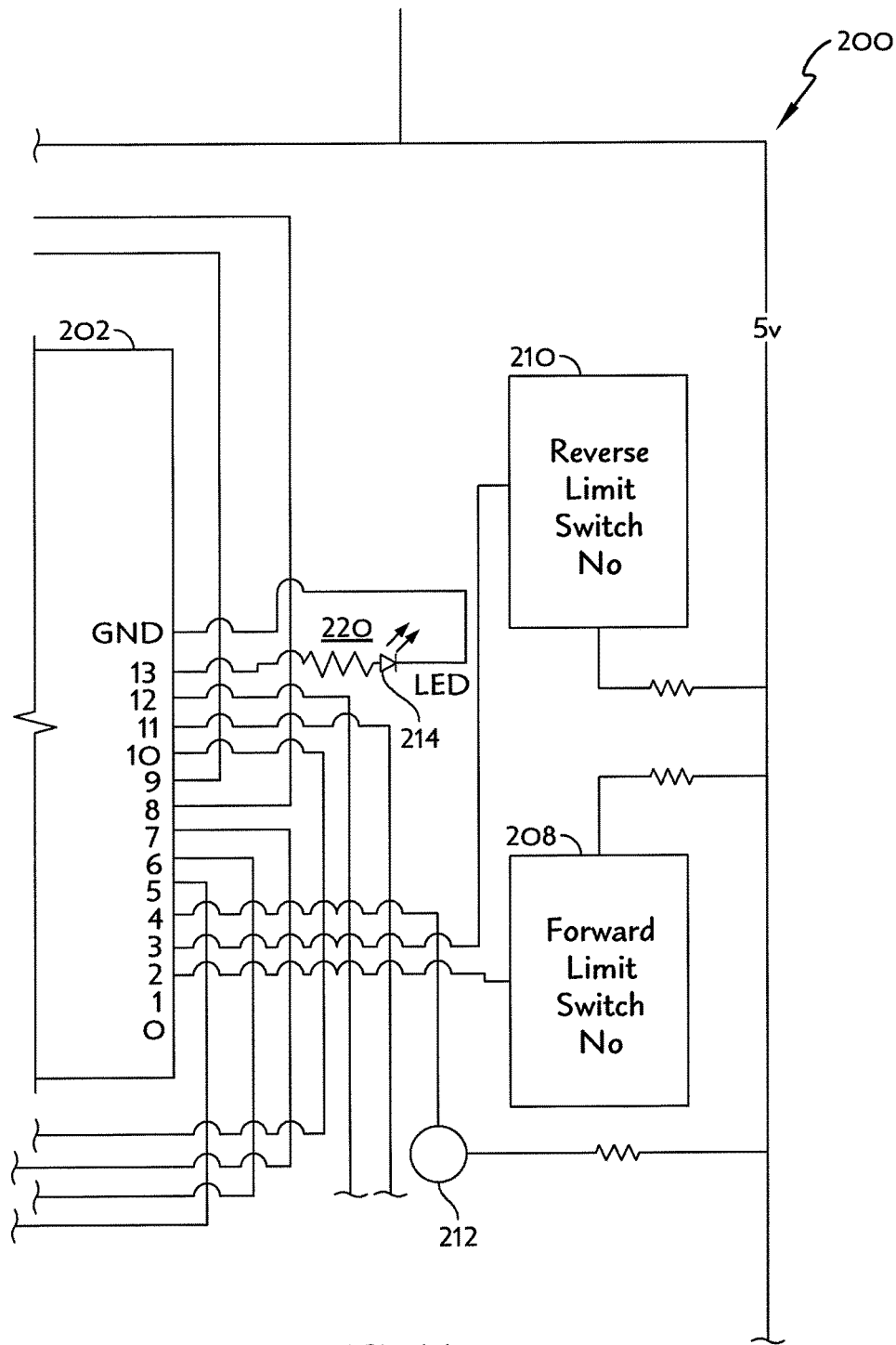

Forward 208 and reverse 210 limit switches, FIG. 14, sense the endpoints of travel of block 120 and thus of plunger 108. Switches 208, 210 illustratively are Yueqing Daier Electron Co., Ltd., model MSW-0 switches. A terminal of switch 208 is coupled through a 10 KΩ resistor to 5V. The other terminal of switch 208 is coupled to pin 2 of µC 202. A terminal of switch 210 is coupled through a 10 KΩ resistor to 5V. The other terminal of switch 210 is coupled to pin 3 of µC 202. A controller 200 START button 212 is coupled in series with a 10 KΩ resistor across pin 4 of µC 202 and 5V. START button 212 illustratively is a Radio Shack model NTE54-394 push button. A controller 200 ON indicator LED 214 is coupled in series with a 220 Ω resistor across pin 13 and a GND terminal of µC 202. LED 214 illustratively is a Radio Shack green LED with holder, model 276-069.

Figure 15:
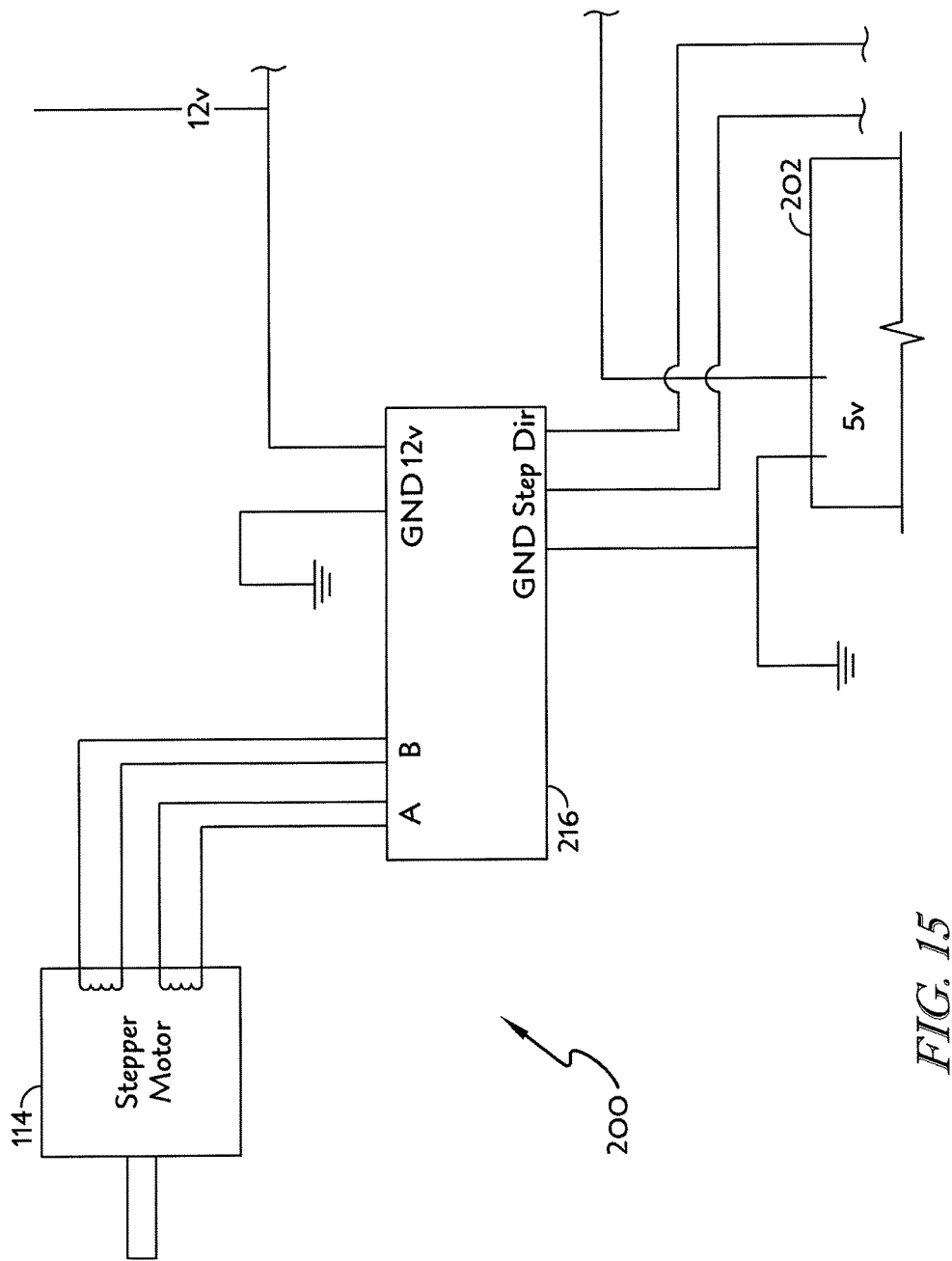
Figure 16:
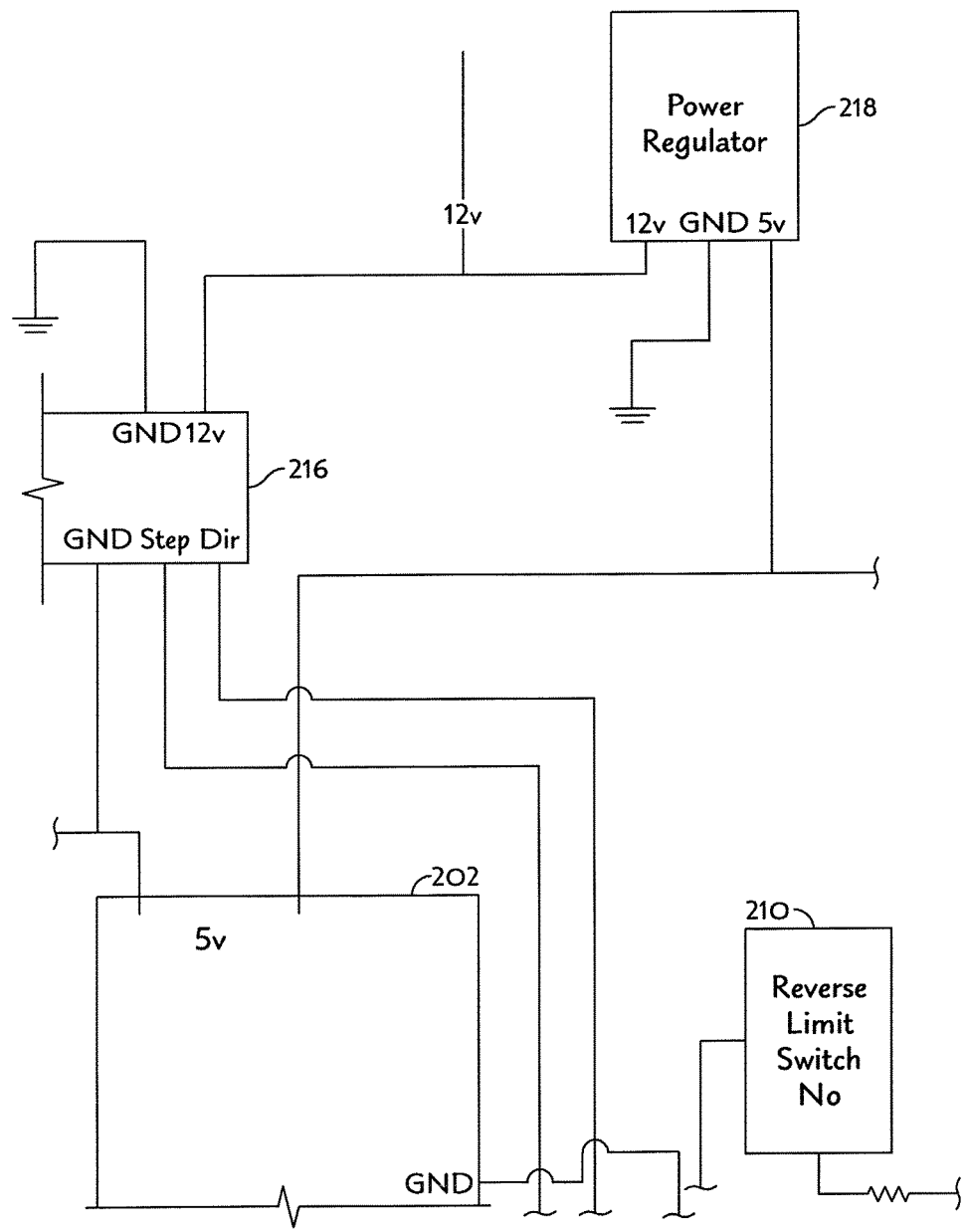
Figure 17:
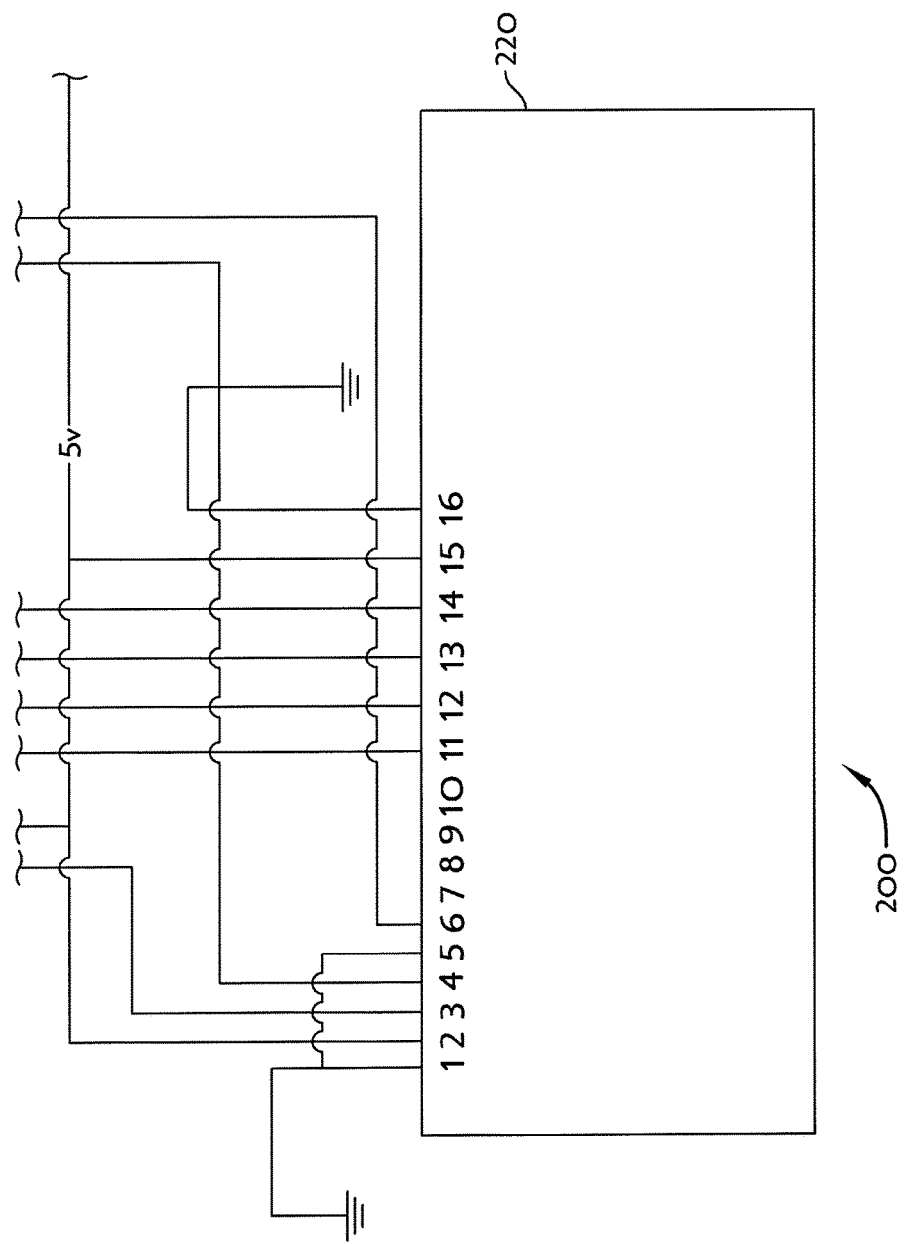

Referring to FIG. 15, the stepper motor 114 is driven from pins 8 and 9 of µC 202 through a motor driver 216, such as a Sparkfun (Schmalzhaus) ROB10267 Easy Driver V4, or an Allegro A3967 driver chip. The GND terminal of the driver 216 is coupled to the GND terminal of the µC 202. Pins 8 and 9 of µC 202 are coupled to pins DIRection and STEP, respectively, of driver 216. Power for the motor 114 is 12 VDC which is coupled to the 12V terminal of driver 216. This voltage is regulated by a 5V power regulator 218, FIG. 16, the 12V terminal of which is also coupled to the 12V terminal of driver 216. The GND terminal of regulator 218 is coupled to ground. The 5V terminal of regulator 218 provides the system 5V supply. Regulator 218 illustratively is a type LM317 power regulator.

Controller 202 status, for example, the pressure being sensed by sensor 204, is displayed on a display 220. Display 220 illustratively is a Hitachi type HD44780 LCD or a Unitech model UC-204A LCD. Pins 1 and 5 of display 220 are coupled to ground. Pins 2 and 3 of display 220 are coupled to two terminals of a 10 KΩ rotary potentiometer 222, FIG. 13. A remaining terminal of potentiometer 222 is coupled to ground. Potentiometer 222 provides contrast control for display 220. Pins 4, 6 and 11-14 of display 220 are coupled to pins 12-10 and 7-5, respectively, of µC 202. Pin 15 of display 220 is coupled to 5V. Pin 16 of display 220 is coupled to ground.

Figure 18:
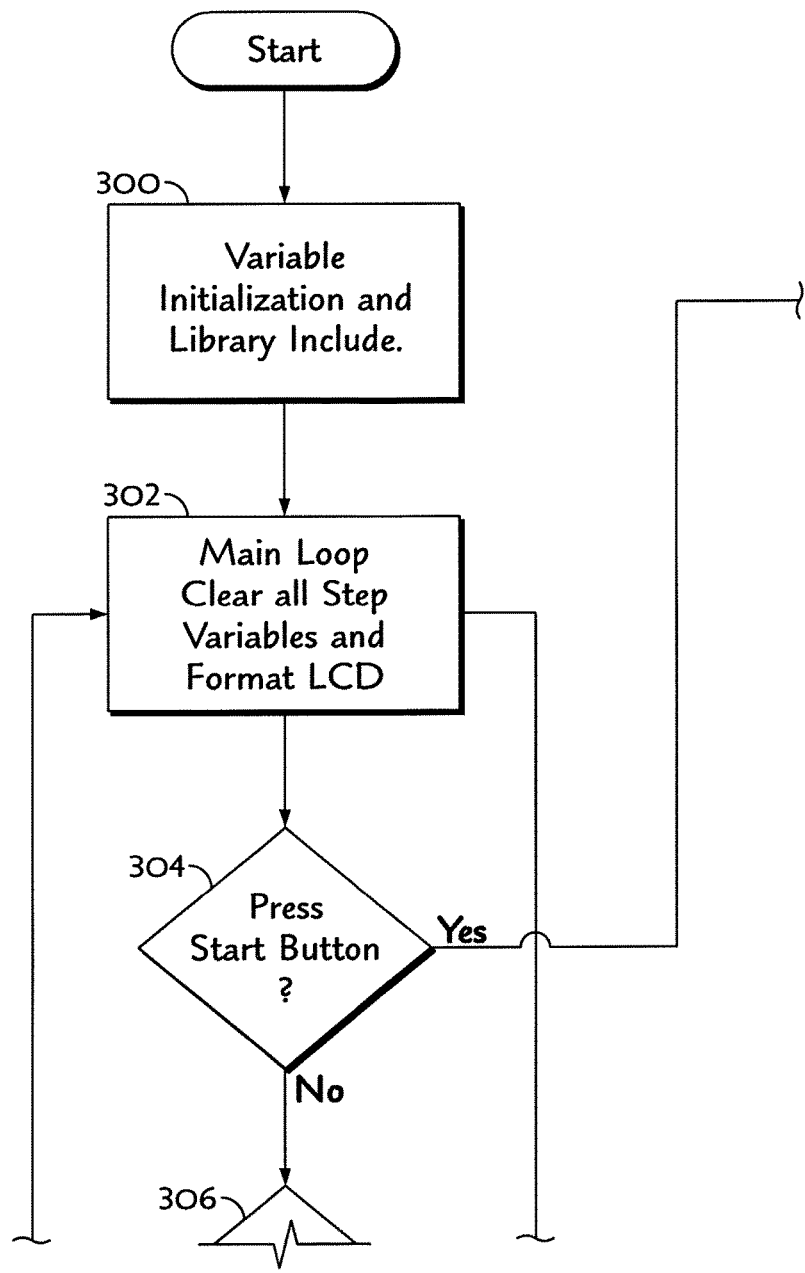
FIGS. 18-21 illustrate a program flow diagram useful to practice the invention.

A flow diagram of the program which controller 200 executes is illustrated in FIGS. 18-21. Referring first to FIG. 18, at step 300, variables, including the library, are initialized. At step 302, all step variables are cleared, and the display 200 is formatted. Referring to both FIGS. 18 and 19, at step 304, "Press start button 212?" is queried. If step 304, "Press start button 212?" is YES, referring to FIG. 20, step 310, "Clear display 220, read sensor 204" is executed. If step 304, "Press start button 212?" is NO, referring to FIG. 19, step 306, "Is linear slide 118 in park?" is queried.

If step 306, "Is linear slide 118 in park?" is YES, step 307, "Flash ready LED 214" is executed and the program returns to FIG. 18, step 302. If step 306, "Is linear slide 118 in park?" is NO, FIG. 19, step 308, "park linear slide 118, display 'Returning' on display 220," is executed, and the program returns to FIG. 18, step 302.

Figure 20:
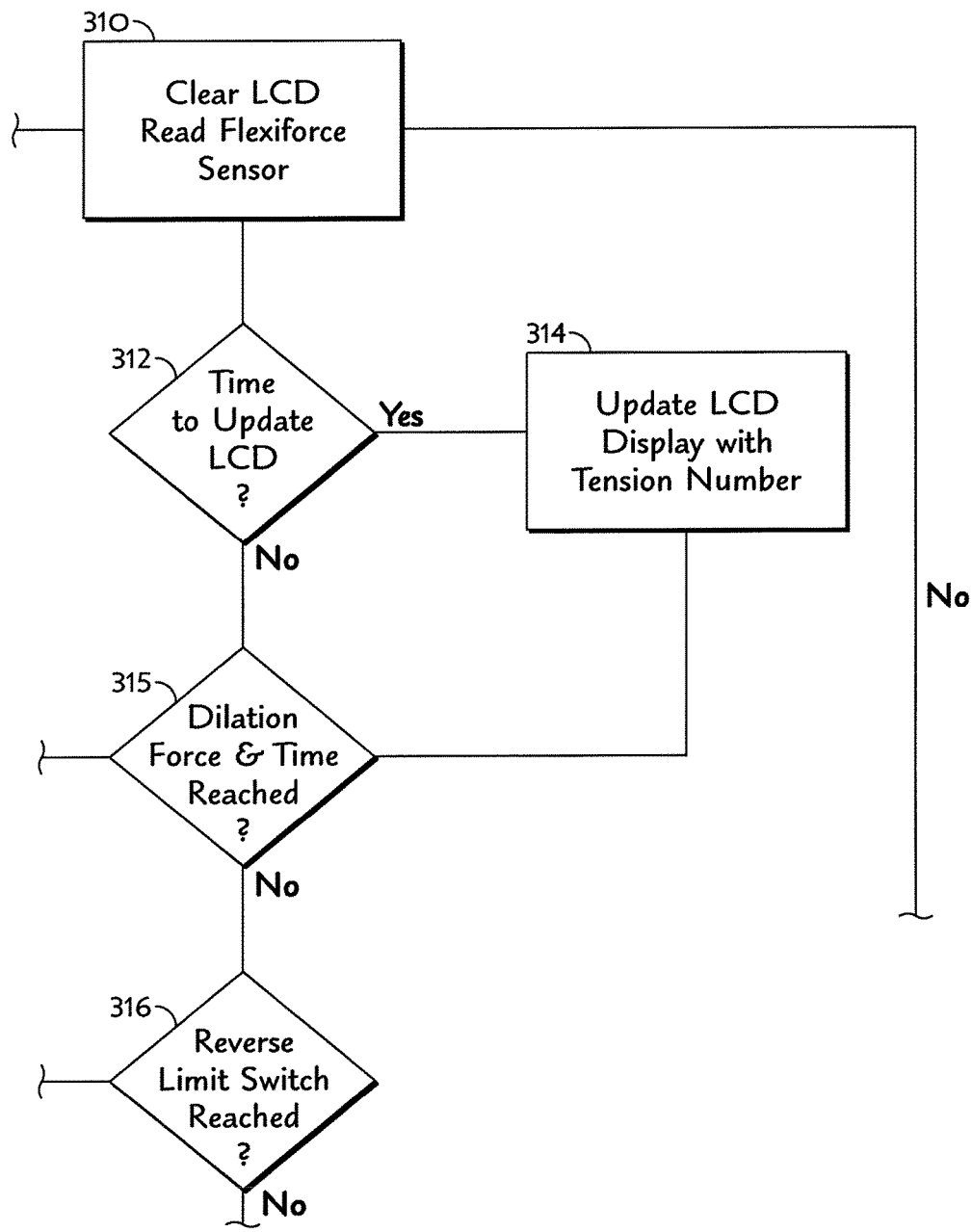

From FIG. 20, step 310, "Clear display 220, read sensor 204," at FIG. 20, step 312, "Time to update display 220?" is queried. If step 312, "Time to update display 220?" is YES. at FIG. 20, step 314, "Update display 220 with sensor 204 reading," is executed, and the program proceeds to FIG. 20, step 315, "Dilation force and time reached?" If step 312, "Time to update display 220?" is NO, the program proceeds to FIG. 20, step 315, "Dilation force and time reached?"

Figure 19:
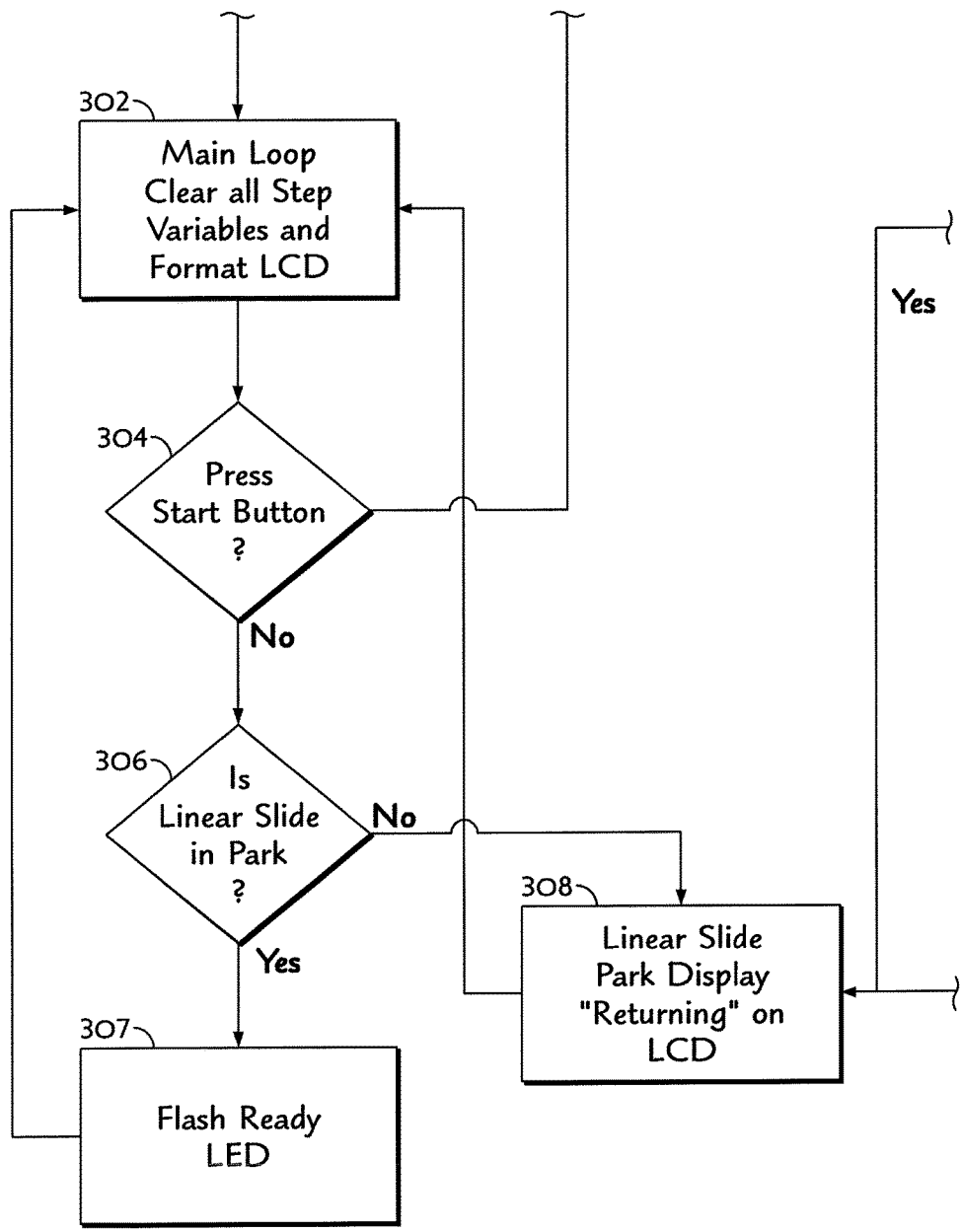

If FIG. 20, step 315, "Dilation force and time reached?" is YES, the program proceeds to FIG. 19, step 308 "park linear slide 118, display 'Returning' on display 220," is executed, and the program returns to FIG. 18, step 302. If FIG. 20, step 315, "Dilation force and time reached?" is NO, the program proceeds to FIGS. 20-21, step 316, "Reverse limit switch 210 reached?"

Figure 21:
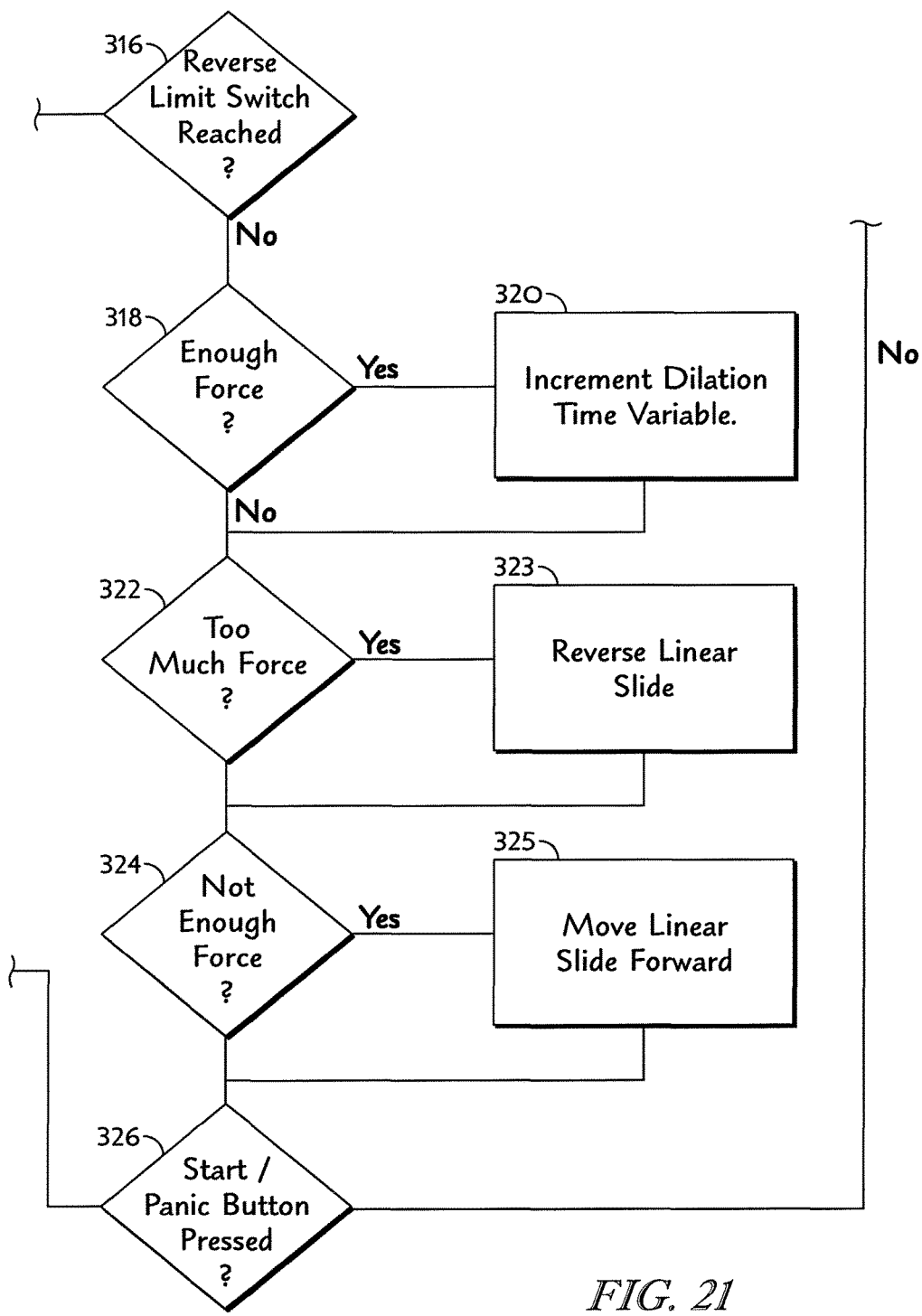
Figure 22:
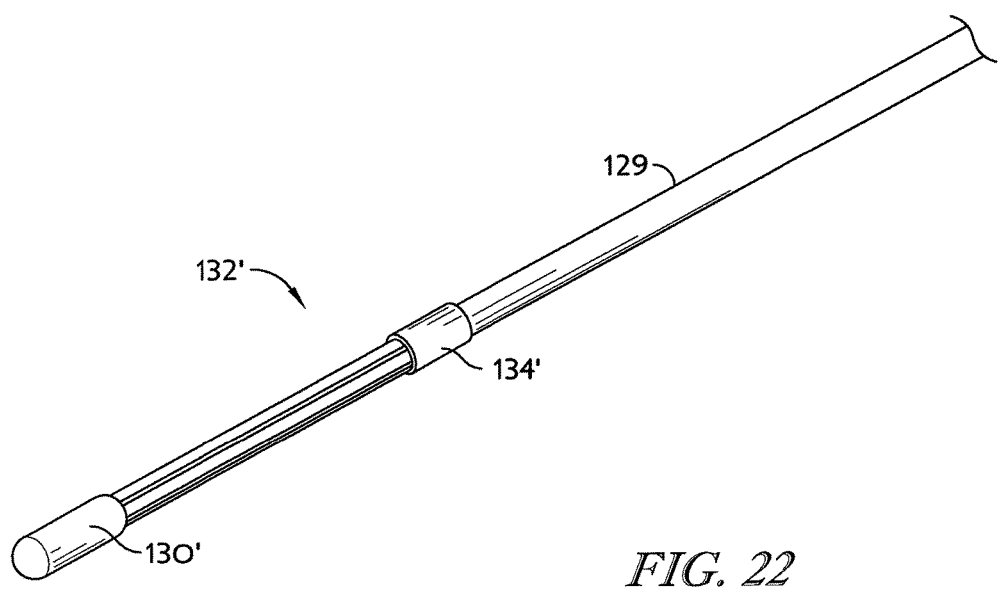
FIG. 22 illustrates an enlarged fragmentary perspective view of another embodiment in an unexpanded condition.
Figure 23:
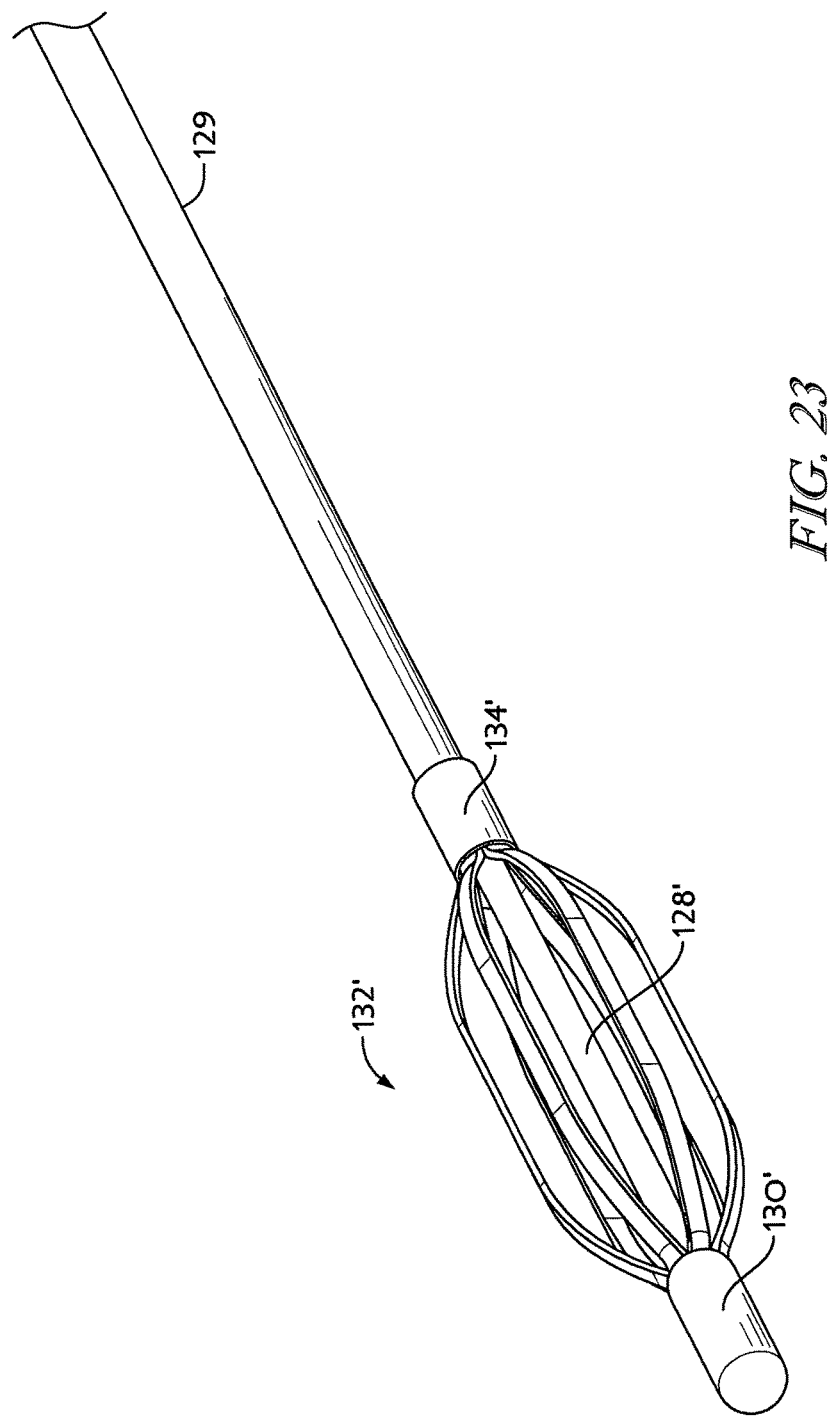
FIG. 23 illustrates the embodiment illustrated in FIG. 22, but in expanded condition; and, FIG. 24 illustrates an enlarged fragmentary perspective view of another embodiment in an expanded condition.

If FIGS. 20-21, step 316, "Reverse limit switch 210 reached?" is YES, the program proceeds to FIG. 19, step 308, "park linear slide 118, display 'Returning' on display 220," and the program returns to FIG. 18, step 302. If "Reverse limit switch 210 reached?" is NO, the program proceeds to FIG. 21, step 318, "Enough force?"

If FIG. 21, step 318, "Enough force?" is YES, the program proceeds to FIG. 21, step 320, "Increment dilation time variable," and then to FIG. 21, step 322, "Too much force?" If FIG. 21, step 318, "Enough force?" is NO, the program proceeds to FIG. 21, step 322 "Too much force?"

If FIG. 21, step 322 "Too much force?" is YES, the program proceeds to FIG. 21, step 323, "Reverse linear slide 118," and then to FIG. 21, step 324, "Not enough force?" If FIG. 21, step 322 "Too much force?" is NO, the program proceeds to FIG. 21, step 324, "Not enough force?"

If FIG. 21, step 324, "Not enough force?" is YES, the program proceeds to FIG. 21, step 325, "Move linear slide 118 forward," and then to FIG. 21, step 326, "Start button 212 pressed?" If FIG. 21, step 324, "Not enough force?" is NO, the program proceeds to FIG. 21, step 326, "Start button 212 pressed?"

If FIG. 21, step 326, "Start button 212 pressed?" is YES, the program proceeds to FIG. 19, step 308, "park linear slide 118, display 'Returning' on display 220," and then to FIG. 18, step 302. If FIG. 21, step 326, "Start button 212 pressed?" is NO, the program proceeds to FIG. 20, step 310, "Clear display 220, read sensor 204."

At the end of the treatment, pressures and durations of each interval of treatment can be transferred to a patient treatment record.

What is claimed is:

1. Apparatus for treating a stricture in a body lumen comprising:
    a device including a balloon catheter configured for exerting pressure on the stricture incrementally to gradually relieve the stricture,
    a controller operable for controlling the amount of pressure the balloon catheter of the device exerts on the stricture, and
    a pressure sensor configured for sensing the pressure being exerted on the stricture by the device, wherein the controller includes a plurality of instructions that, when executed by the controller, cause the controller to:
    (a) sense pressure exerted by the device on the stricture,
    (b) determine if enough force is being exerted on the stricture,
    (c) if enough force is being exerted, time with the controller the application of enough force,
    (d) determine if too much force is being exerted by the treatment device on the stricture,
    (e) if too much force is being applied to the stricture, automatically decrement the force being applied to the stricture,
    (f) determine if not enough force is being applied to the stricture,
    (g) if not enough force is being applied to the stricture, automatically increment the force being applied to the stricture, and
    (h) automatically repeat (a)-(g) until, a desired pressure has been maintained on the stricture for a desired time to gradually relieve the stricture and widen the body lumen.

2. The apparatus of claim 1, wherein the device includes a syringe, a motor, a screw coupled to the motor, and a follower for following rotation of the screw to advance and retract a plunger of the syringe to increase and decrease, respectively, the pressure of the inflating fluid in the balloon.

3. The apparatus of claim 1 wherein the device includes a limit switch to limit the pressure exerted by the device on the stricture.

* * * * *